United States Patent [19]

Bajek

[11] B 3,999,959

[45] Dec. 28, 1976

[54] MOTOR FUEL BLENDING CONTROL SYSTEM

[75] Inventor: Walter A. Bajek, Lombard, Ill.

[73] Assignee: Universal Oil Products Company, Des Plaines, Ill.

[22] Filed: Aug. 12, 1974

[21] Appl. No.: 496,792

[44] Published under the second Trial Voluntary Protest Program on February 17, 1976 as document No. B 496,792.

[52] U.S. Cl. .................................. 44/2; 208/17; 23/230 A
[51] Int. Cl.² .................. C10L 1/04; C10L 1/10; G01N 33/00
[58] Field of Search ........... 44/2; 23/230 A; 208/17

[56] References Cited

UNITED STATES PATENTS

| | | |
|---|---|---|
| 3,383,190 | 5/1968 | Weber et al. ........................ 44/2 |
| 3,385,680 | 5/1968 | Feld et al. ........................... 44/2 |
| 3,437,461 | 4/1969 | Hoffman et al. ..................... 44/2 |
| 3,533,746 | 10/1970 | Fenske ............................ 23/230 A |

Primary Examiner—Carl F. Dees
Attorney, Agent, or Firm—James R. Hoatson, Jr.; Robert W. Erickson; William H. Page, II

[57] ABSTRACT

At least two gasoline streams, having dissimilar octane ratings, are admixed with a butane-rich stream, the latter for vapor pressure control. A control system is employed to regulate the quantity of a lead-containing compound and/or the relative quantities of the blend components to achieve both the target octane of the final motor fuel blend as well as the desired vapor pressure, or volatility.

9 Claims, 1 Drawing Figure

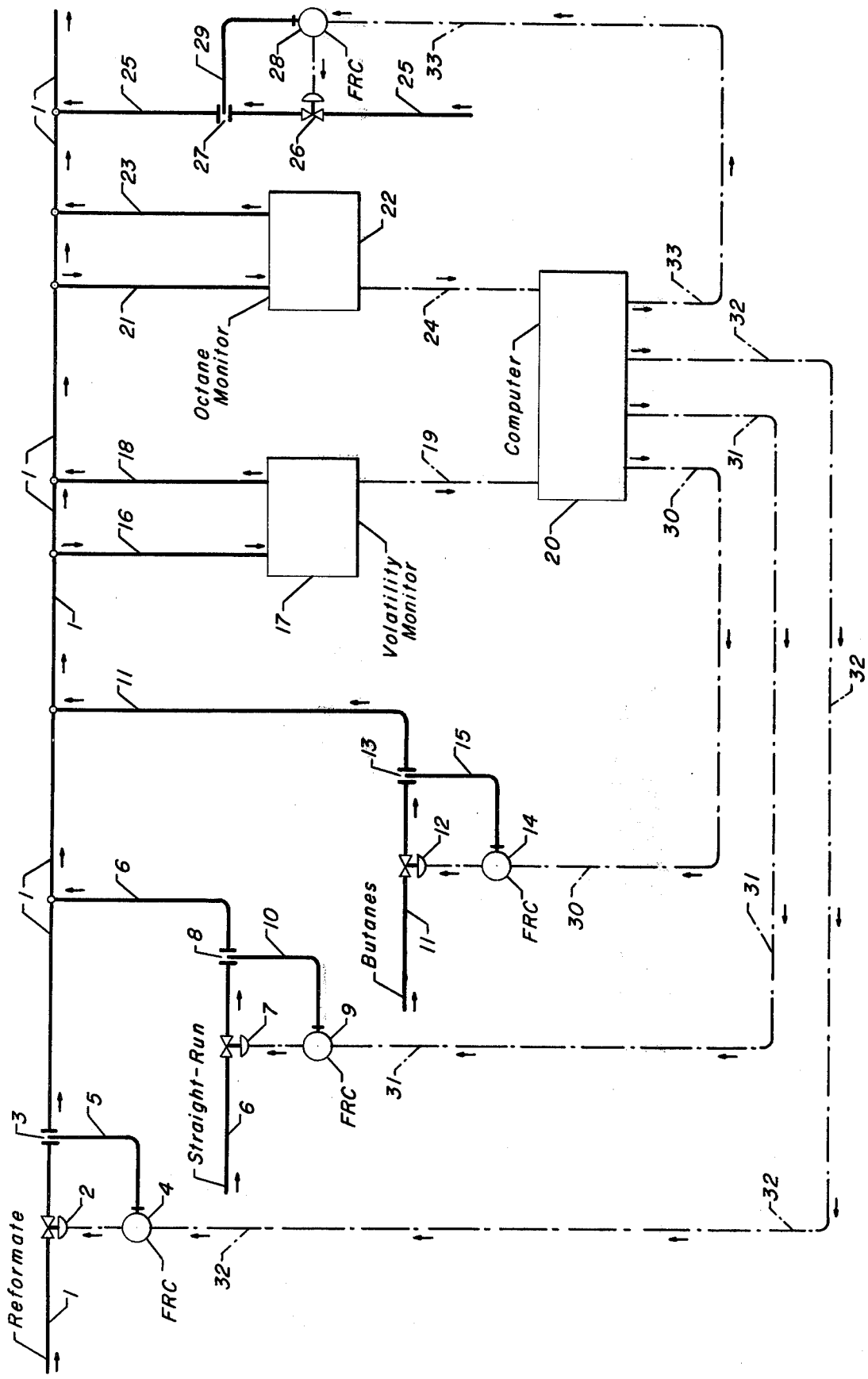

MOTOR FUEL BLENDING CONTROL SYSTEM

APPLICABILITY OF INVENTION

The present invention is directed toward the blending of various gasoline streams, which result from a variety of petroleum processes, to produce what is commonly referred to as the "refinery octane pool". Marketing demands, as well as automotive requirements, generally dictate the production of both a "regular" grade gasoline pool and a "premium" grade gasoline pool. Relatively recent concern over the violence perpetrated upon the atmosphere, via vehicular exhaust, has given rise to a third gasoline pool, the "low-lead" pool. These three grades of motor fuel contain varying quantities of lead-containing compound — e.g. tetraethyl lead (TEL), or tetramethyl lead (TML); low-lead contains from about 0.01 to about 1.0 cc. TEL/gal., regular from about 0.5 to about 2.0 cc./gal. and premium from about 1.5 to a maximum of about 3.0 cc./gal. Regardless of the particular grade, the quantity of the lead-containing compound, required to attain the target octane rating of the final blend, is principally dependent upon the ratings of the individual blend components and the chemical character of the hydrocarbons therein.

In addition to the final octane rating of the ultimate motor fuel blend, the refiner must direct his attention to the vapor/liquid ratio, or the vapor pressure thereof. One principal consideration in this regard is the locale in which the products are destined to be marketed. In a warm, or temperate climate, the vapor pressure can be lower than is necessary in a comparatively cold climate. In motor fuel blending operations, the most common technique, to achieve the desired vapor pressure, or vapor/liquid ratio is the addition of a butane-rich stream which, in view of various operating parameters within the refinery, will contain a comparatively low concentration of pentanes.

The control system encompassed by my invention considers the effect of the octane blending values of the various gasoline streams, that of the butane-rich stream, and, in response thereto, regulates the quantity of lead-containing compound required to attain the target octane rating for that particular refinery pool.

OBJECTS AND EMBODIMENTS

A principal object of my invention is to provide a control system for the motor fuel blending of at least two gasoline fractions having dissimilar octane ratings. A corollary objective is to afford a greater degree of uniformity to the refinery octane pool through rapid, continuous analysis accompanied by virtually immediate compensation for changes in the blend components.

Another object resides in the capability of minimizing the quantity of expensive lead-containing compounds required to achieve the desired octane rating of the final blended motor fuel, or the give-away of higher octane material in low-lead or clear blends.

In one embodiment, therefore, my invention encompasses a control system for use in a process for motor fuel blending, wherein two gasoline streams, having dissimilar octane ratings, are admixed and (i) a butane-rich stream is added for vapor pressure control, and (ii) a lead-containing compound is added to increase the octane rating of the motor fuel blend, which control system comprises, in cooperative combination: (a) first flow-varying means for adjusting the flow rate of the gasoline stream having the higher octane rating; (b) second flow-varying means for adjusting the flow rate of the gasoline stream having the lower octane rating; (c) third flow-varying means for adjusting the flow rate of said butane-rich stream; (d) a first hydrocarbon analyzer receiving a sample of the blend of said butane stream, said higher octane gasoline stream and said lower octane stream, and developing a first output signal representative of a composition characteristic of said sample; (e) a second hydrocarbon analyzer receiving a second sample of said blend, and developing a second output signal representative of the octane rating of said sample; (f) comparator means, receiving said first and second output signals, which compares the rate of change thereof and the actual value of the octane rating of said blend, and generates third and fourth output signals; (g) fourth flow-varying means for adjusting the flow rate of said lead-containing compound added to said blend; (h) first signal-receiving means to which said third output signal is transmitted by said comparator means, said first signal-receiving means in turn transmitting to said fourth flow-varying means, whereby the flow of said lead-containing compound is adjusted in response to said octane rating; and, (i) second signal-receiving means to which said fourth output signal is transmitted by said comparator means, said second signal-receiving means in turn transmitting to said third flow-varying means, whereby the flow of said butane stream is adjusted in response to said composition characteristic.

In another embodiment, the present invention is directed toward a process for blending motor fuel which comprises the steps of: (a) admixing a butane-rich stream with a first gasoline stream, having a relatively high octane rating, and a second gasoline stream, having a lower octane rating; (b) regulating the flow rates of said first and second gasoline streams, and said butane-rich stream by adjusting first, second and third flow-varying means; (c) introducing a first sample of the resulting motor fuel blend into a first hydrocarbon analyzer and developing therein a first output signal representative of a composition characteristic of said sample; (d) introducing a second sample of the resulting motor fuel blend into a second hydrocarbon analyzer and developing therein a second output signal representative of the octane rating thereof; (e) transmitting said first and second output signals to comparator means, which compares the rate of change thereof and the actual value of the octane rating of said second sample, and generating therein third, fourth, fifth and sixth output signals; (f) admixing a lead-containing compound with said motor fuel blend, regulating the flow of said compound by fourth flow-varying means; (g) transmitting said third output signal to said fourth flow-varying means, whereby the flow of said lead-containing compound is adjusted in response to said octane rating; and, (h) transmitting at least one of said fourth, fifth and sixth output signals to at least one of said first, second and third flow-varying means, whereby the flow of at least one of said first and second gasoline streams, and said butane-rich stream is adjusted in response to said octane rating, or said composition characteristic.

Other objects and embodiments of the present invention will be evident from the following detailed description thereof. In one such other embodiment, the second hydrocarbon analyzer comprises a stabilized cool flame generator having a servo-positioned flame front.

PRIOR ART

Candor compels recognition of the fact that the integration and utilization of sophisticated control systems in a petroleum refining process are generally considered to be among recent technological innovations. For example, U.S. Pat. No. 3,759,820 (Cl. 208–64) discusses the systematized control of a multiple reaction zone process in response to two different quality characteristics of the ultimately desired product. U.S. Pat. No. 3,649,202 (Cl. 23–253A) involves the control of reaction zone severity in response to the octane rating of the normally liquid product effluent, and is primarily directed toward the well known and thoroughly documented catalytic reforming process. Other instances of the integration of control systems into various segments of petroleum refining processes are found in U.S. Pat. Nos. 3,751,229 (CL. 23–253A), 3,738,448 (Cl. 235–151.12) and 3,756,921 (Cl. 196–132).

Similarly, the present control system is intended for utilization in a petroleum refinery, but not in conjunction with a particular refining process. Rather, my invention serves to alleviate the problems attendant motor fuel blending for octane rating and volatility control. There is afforded a greater degree of uniformity, with respect to the particular octane pool, through continuous monitoring followed by virtually immediate compensation for physical and/or chemical changes in the components of the blend.

SUMMARY OF INVENTION

In a complete refinery, the various octane pools constitute a variety of gasoline streams from a multitude of sources. One such source is the light straight-run-naphtha fraction recovered as an overhead stream from the crude oil distillation column. This gasoline stream, having a boiling range from about 80°F. to about 230°F., generally exhibits a clear research octane blending value of about 75.0 to about 80.0. Other sources include a light hydrocracked naphtha fraction having a research octane rating of about 84.7; the liquid product from a catalytic reforming unit, having a research octane rating of about 90.0 to about 92.0, or more depending upon operating severity; a catalytically cracked gasoline stream, having a research octane rating of about 94.0; alkylate gasoline, having an octane rating of about 92.0 to about 97.0; and, a mixed butane stream, having an octane rating from about 90.0 to about 100.2. It will be recognized that the butane-rich stream utilized for vapor pressure control of the gasoline pool, will also have an effect upon the ultimate octane rating thereof. In those instances where the desired end result is a low-lead gasoline pool, a normal pentane/normal hexane concentrate, from one or more of the conversion processes within the refinery, will be processed to produce isomeric pentanes and hexanes having an average clear octane rating of about 90.5.

In addition to the butane-rich stream employed to obtain the desired vapor pressure, at least two of the above-described gasoline streams will form the greater proportion of refinery octane pools. For illustration purposes, and to simplify the continuing discussion of the present invention, it will be presumed that the particular gasoline pool will consist of a mixture of light straight-run gasoline and the normally liquid product effluent emanating from a catalytic reforming unit. It is understood, however, that there is no intent to so limit the control system of the present invention. With respect to the number of component streams making up the final motor fuel blend, it will be recognized that the problems and difficulties attendant manual control, via indirect analysis of the component streams, and ultimate octane rating, are multiplied as the number of component streams is increased. Since, in the greater majority of situations, some quantity of a lead-containing compound will be added to the motor fuel blend to achieve a desired octane rating, still another aspect contributes to the difficulties attendant present-day control techniques. In accordance with the control technique of the present invention, samples of the unleaded motor fuel blend, inclusive of the butane-rich stream, are introduced into hydrocarbon analyzers which produce output signals. These output signals are transmitted to comparator means which compares the rate of change thereof and the actual value of the octane rating of the unleaded blend, and generates additional output signals. The latter are utilized to determine the quantity of the lead-containing compound required to achieve the target octane of the final motor fuel blend and to increase or decrease the rate of flow of the component gasoline streams as is necessary. This manner of octane rating control effectively "saves" valuable high octane components and continuously minimizes the required quantity of the expensive lead-containing compound.

HYDROCARBON ANALYZERS

The control system of the present invention utilizes at least two hydrocarbon analyzers. One of these develops an output signal which is corollatable with the octane rating of the unleaded blend of gasoline component streams. Complete details of this hydrocarbon analyzer, herein referred to as an "octane monitor", may be obtained upon reference to U.S. Pat. No. 3,463,613 (Cl. 23–230). As stated therein, a composition characteristic of a hydrocarbon sample can be determined by burning the same in a combustion tube under conditions which generate a stabilized cool flame. The position of the flame front is automatically detected and employed to develop a signal which, in turn, is employed to vary a combustion parameter, such as combustion pressure, induction zone temperature or air flow, in a manner which immobilizes the flame front regardless of changes in the composition characteristic of the hydrocarbon sample. The change in the combustion parameter, required to immobilize the flame following a change of sample composition, is corollatable with the composition characteristic change. An appropriate read-out device, connecting therewith, may be calibrated in terms of the desired identifying characteristic such as the octane rating.

The hydrocarbon analyzer is conveniently identified as comprising a stabilized cool flame generator with a servo-positioned flame front. The type of analysis effected thereby is not a compound-by-compound analysis such as presented by instruments including mass spectrometers, or vapor phase chromatographs, which can be used as hereafter stated. On the contrary, the analysis is represented by a continuous output signal which is responsive to and indicative of hydrocarbon composition and, more specifically, is corollatable with one or more conventional identifications or specifications of petroleum products such as Reid vapor pressure, ASTM or Engler distillations, boiling points, or, for motor fuels, anti-knock characteristics such as research octane number, motor octane number, or a composite of such octane numbers.

Other examples of cool flame generators, having servo-positioned flame fronts, and their uses in analyzing hydrocarbon compositions and monitoring the same, are illustrated in U.S. Pat. Nos. 3,533,745 (Cl. 23–230), 3,533,746 (Cl. 23–230) and 3,533,747 (Cl. 23–230). It is this type of hydrocarbon analyzer which is preferred for use as the octane monitor, although it is suitable for analyzing various boiling characteristics of the gasoline streams for the purpose of monitoring and controlling the vapor pressure (volatility) of the final blended product. As hereinbefore stated, the vapor pressure is controlled by monitoring the flow rate of the butane-rich stream in the unleaded gasoline blend, and a second sample thereof is introduced into a second hydrocarbon analyzer. Although the analyzer employed to produce the output signal, which is representative of the octane number of the blend, may be used to analyze the second sample, it will be preferred, in many instances, to utilize one adapted to various boiling characteristics of gasoline streams. Such boiling characteristics include boiling points, vapor/liquid ratios at various temperatures, vapor pressure, molecular weight, etc. Thus, the second hydrocarbon analyzer may incorporate a gas-liquid chromatographic column as disclosed in U.S. Pat. Nos. 3,097,517 (Cl. 73–23) and 3,257,847 (Cl. 73–23.1).

A continuous vapor/liquid ratio analyzer is described in U.S. Pat. No. 3,491,585 (Cl. 53–23). A particularly preferred method for maintaining the predetermined volatility ASTM is thoroughly described in U.S. Pat. No. 3,813,925 (Cl. 73–64.2). Briefly, as detailed therein, ASTM standard methods exist by which the vapor/liquid ratios at various temperatures can be determined. The importance of this ratio resides in its use as a specification for motor fuel quality as limiting its tendency to cause vapor lock in internal combustion engines. The V/L ratio of 20 has been selected as the standard, and the temperature at which this V/L ratio is exhibited is utilized as the grading system for volatility. The specified temperatures are based upon expected ambient temperatures in the locale of ultimate use, and the current ASTM standards require one of the following: 105° F., 116° F., 124° F., 133° F., or 140° F. In gasoline blending, the V/L ratio is generally controlled through the regulation of butane content of the final blend.

In accordance with the continuous analyzer, if the V/L ratio determined by the controller is less than that desired, the heat input to the vapor-liquid separation zone will be increased, thereby increasing the amount of vaporization. The temperature at which the V/L ratio of the gasoline blend equals 20 is, therefore, obtained by monitoring the separation zone temperature after the system has attained a steady-state condition. This temperature is then compared with the specified standard temperature for the desired volatility of the gasoline. The difference between the two temperatures is converted into a required increase or decrease in butane addition. An indicated temperature above the standard requires that an increase in butane addition be made to increase the volatility of the blend. This will result in a decrease in the indicated temperature.

As hereinbefore stated in one of the specific embodiments, the control system will further include computer-comparator means which receives the output signals from the hydrocarbon analyzers, and compares the rate of change and actual values of the composition characteristics. The comparator, or computer, having been programmed to select a blend having minimal cost while meeting the specifications as to final octane rating and volatility, generates numerous output signals, one each for each blend component and one for regulating the addition of the lead-containing compound. These additional output signals are transmitted to various signal-receiving means, or flow control means, to reset the set points thereof in response to successive comparisons. It may be that any one, or more of these output signals will indicate that no change is then necessary. The flow control means in turn transmit the appropriate signals to flow-varying means whereby the flow of gasoline component streams, the butane-rich stream and/or the lead-containing compound is adjusted in response thereto.

Second comparator means can be included in the control system for comparing the actual value of the composition characteristics, or of the various flow rates, with previously determined deviation limits and for generating any necessary adjustment signals in response to this comparison. When the value, for example with respect to lead addition, lies beyond the preset limits, and the rate of change with respect to time indicates that the value will continue to depart from such limits, the second comparator means will generate one or more adjustment signals.

In further describing my invention, reference will be made to the accompanying drawing which is presented for the sole purpose of illustration, and not with the intent of unduly limiting the present invention beyond the scope and spirit of the appended claims. The gasoline blending control system is presented by means of a simplified flow diagram in which hydrocarbon analyzers 17 and 22, and computer (or comparator) 20 are conveniently shown as labeled boxes. The precise construction of these devices is not considered essential to the present invention; many designs, for effecting the desired functions in accordance with the description herein set forth, are available, and will be recognized as suitable by those possessing the requisite skill in the appropriate art.

DESCRIPTION OF DRAWING

Illustrated is a simple, but common situation wherein a petroleum refiner has available two gasoline streams, the normally liquid (pentanes and heavier) product emanating from a catalytic reforming unit and a light straight-run gasoline from a crude column. The unleaded research octane ratings of these streams varies from about 89.5 to about 92.5, and from about 74.8 to about 80.5, respectively. A mixed butane stream, having an unleaded research octane rating in the range of about 89.9 to about 100.0, is utilized for vapor pressure control as defined by the ASTM specifications regarding the temperature at which the vapor/liquid ratio of the final blended product is 20.

With reference now to the drawing, the catalytic reformate is transported to the tank farm via line 1, the flow rate thereof being varied by control valve 2. Control valve 2 is actuated via Flow Recorder Controller (FRC) 4 which monitors the flow through line 1 by way of orifice meter 3 and line 5. The catalytic reformate continues through line 1 wherein it is admixed with the light straight-turn gasoline stream introduced via line 6, the flow rate of which is varied by control valve 7. The latter regulates the flow rate of the straight-run stream upon a signal received from FRC 9 which senses the flow via orifice meter 8 and line 10. The mixed gasoline stream continues through line 1, into which a mixed butane stream is added by way of line 11, the flow thereof being varied by control valve 12 which is actuated by a signal received from FRC 14. The latter monitors the butane flow in line 11 via orifice meter 13 and line 15.

The butane-blended gasoline mixture continues through line 1 with tetraethyl lead being added thereto via line 25. The flow rate of the lead-containing compound is varied by control valve 26 which is actuated by a signal from FRC 28; the latter senses the tetraethyl lead flow by way of orifice meter 27 and line 29.

Prior to the addition of tetraethyl lead to the gasoline blend, two samples are withdrawn from line 1 through lines 16 and 21. The first sample is introduced into volatility monitor 17. The sample system generally comprises a closed loop removing about 100 cc./min. via line 16, and returning the excess via line 18; the required quantity of sample is injected into monitor 17, from an intermediate point, by a metering pump not illustrated. The second sample, from line 21, is introduced into octane monitor 22, with the excess sample being returned via line 23.

Octane monitor 22 is field-installed adjacent blend line 1; it utilizes a stabilized cool flame generator having a servo-positioned flame front. The flow of oxidizer (air) and fuel (the blend sample from line 21) are fixed, as is the induction zone temperature. Combustion pressure is the parameter which is varied in such a manner that the stabilized cool flame front is immobilized. Upon experiencing a change in unleaded octane rating, the change in pressure required to immobilize the flame front within the octane monitor provides a direct indication of the change. Typical operating conditions for octane monitor 22 are: air flow, 3,500 cc./min. (STP); fuel flow, 1.0 cc./min.; induction zone temperature (research octane), 700°F.; combustion pressure, 4.0 to 20.0 psig.; and, octane number range, 80 to 102.

Volatility monitor 17 is preferably of the type described in U.S. Pat. 3,813,925 (Cl. 73–64.2), which monitors the temperature at which the V/L ratio of the unleaded gasoline blend is 20. The obtained temperature is then compared with the ASTM specified standard for the particular locale, and the difference in temperatures is converted into the appropriate signal which dictates either an increase, or a decrease in butane addition. Where the indicated temperature is above the standard, the volatility (V/L ratio) is too low, and an increase in butane addition will be called for; the net result will be a corresponding decrease in the indicated temperature at which the V/L ratio equals 20.

Volatility monitor 17 generates an output signal representative of the V/L ratio of the blend, and transmits the same via instrument line 19 into computer (comparator means) 20. Similarly, octane monitor 22 generates a signal which is representative of the blended octane rating, and transmits the same via instrument line 24. In the present illustration, computer 20 is programmed to generate up to four additional output signals as required (1) to bring the volatility of the blended gasoline within the desired specification and (2) to increase, or decrease the quantity of tetraethyl lead addition in order to meet the intended target octane rating of the gasoline pool. The generated signals are transmitted via instrument lines 30, 31, 32 and 33, to FRC's 14, 9, 4 and 28, respectively. The set points on these FRC's are thereby reset which, in turn, effects the actuation of one or more of the control valves 12, 7, 2 and 26.

The benefits afforded, through the use of this control system, in achieving the desired blend at minimal cost will immediately be recognized. For example, at any given instance, the situation could develop where the combined volatility and octane rating signals will ultimately call for tetraethyl lead addition to a degree exceeding the maximum for a given gasoline pool — e.g., more than 3.0 cc. TEL/gal. The comparator means will create the necessary adjustment signals whereby the relative quantities of the two gasoline streams are properly adjusted. The control system, as illustrated and described lends itself to modifications whereby more accurate and economical results are achieved. For example, additional hydrocarbon analyzers could be used on the individual component gasoline streams to generate additional signals representative of, for example, hydrocarbon composition, octane ratings, etc. Such a technique would permit consideration, by the comparator means, of the "lead response" exhibited by the component streams.

I claim as my invention:

1. In a process for motor fuel blending, wherein two gasoline streams, having dissimilar octane ratings, are admixed and (i) a butane-rich stream is added for vapor pressure control, and (ii) a lead-containing compound is added to increase the octane rating of the motor fuel blend, the control system which comprises, in cooperative combination:
   a. first flow-varying means for adjusting the flow rate of the gasoline stream having the higher octane rating;
   b. second flow-varying means for adjusting the flow rate of the gasoline stream having the lower octane rating;
   c. third flow-varying means for adjusting the flow rate of said butane-rich stream;
   d. a first hydrocarbon analyzer receiving a sample of the blend of said butane stream, said higher octane gasoline stream and said lower octane stream, and developing a first output signal representative of a volatility characteristic of said sample;
   e. a second hydrocarbon analyzer receiving a second sample of said blend, and developing a second output signal representative of the octane rating of said sample;
   f. comparator means, receiving said first and Prepolymer output signals, which compares the rate of change thereof and the actual value of the octane rating of said blend, and generates third and fourth output signals;
   g. fourth flow-varying means for adjusting the flow rate of said lead-containing compound added to said blend;
   h. first signal-receiving means to which said third output signal is transmitted by said comparator means, said first signal-receiving means in turn transmitting to said fourth flow-varying means, whereby the flow of said lead-containing compound is adjusted in response to said octane rating; and,
   i. second signal-receiving means to which said fourth output signal is transmitted by said comparator means, said second signal-receiving means in turn transmitting to said third flow-varying means whereby the flow of said butane stream is adjusted in response to said composition characteristic.

2. The control system of claim 1 further characterized in that said comparator means generates a fifth output signal which is transmitted to third signal-receiving means, said third signal-receiving means in turn transmitting to said first flow-varying means, whereby the flow of said higher octane gasoline stream is adjusted in response to said octane rating.

3. The control system of claim 1 further characterized in that said comparator means generates a sixth output signal which is transmitted to fourth signal-receiving means, said fourth signal-receiving means in turn transmitting to said second flow-varying means, whereby the flow of said lower octane gasoline stream is adjusted in response to said octane rating.

4. The control system of claim 1 further characterized in that said second hydrocarbon analyzer comprises a stabilized cool flame generator having a servo-positioned flame front.

5. The control system of claim 1 further characterized in that said first output signal is representative of the boiling point of said blend.

6. The control system of claim 1 further characterized in that said first output signal is representative of the vapor/liquid ratio of said sample.

7. A process for blending motor fuel which comprises the steps of:
   a. admixing a butane-rich stream with a first gasoline stream, having a relatively high octane rating, and a second gasoline stream, having a lower octane rating;
   b. regulating the flow rates of said first and second gasoline streams, and said butane-rich stream by adjusting first, second and third flow-varying means;
   c. introducing a first sample of the resulting motor fuel blend into a first hydrocarbon analyzer and developing therein a first output signal representative of a volatility characteristic of said sample;
   d. introducing a second sample of the resulting motor fuel blend into a second hydrocarbon analyzer and developing therein a second output signal representative of the octane rating thereof;
   e. transmitting said first and second output signals to comparator means, which compares the rate of change thereof and the actual value of the octane rating of said second sample, and generating therein third, fourth, fifth and sixth output signals;
   f. admixing a lead-containing compound with said motor fuel blend, regulating the flow of said compound by fourth flow-varying means;
   g. transmitting said third output signal to said fourth flow-varying means, whereby the flow of said lead-containing compound is adjusted in response to said octane rating; and,
   h. transmitting at least one of said fourth, fifth and sixth output signals to at least one of said first, second and third flow-varying means, whereby the flow of at least one of said first and second gasoline streams, and said butane-rich stream is adjusted in response to said octane rating, or said composition characteristic.

8. The process of claim 7 further characterized in that said first output signal is representative of the boiling point of said blend.

9. The process of claim 7 further characterized in that said first output signal is representative of the vapor/liquid ratio of said blend.

* * * * *